United States Patent [19]

Subissi

[11] Patent Number: 4,603,132

[45] Date of Patent: Jul. 29, 1986

[54] PHENOTHIAZINE COMPOUNDS WITH ANTI-BRONCHOSPASTIC ACTIVITY AND PHARMACEUTICAL COMPOSITIONS CONTAINING THEM

[75] Inventor: Alessandro Subissi, Pisa, Italy

[73] Assignee: Laboratori Guidotti S.p.A., Pisa, Italy

[21] Appl. No.: 710,022

[22] Filed: Mar. 11, 1985

[30] Foreign Application Priority Data

Mar. 16, 1984 [IT] Italy .............................. 20082 A/84

[51] Int. Cl.$^4$ ..................... A61K 31/54; C07D 279/10
[52] U.S. Cl. ........................................ 514/224; 544/43
[58] Field of Search ........................... 544/43; 514/224

[56] References Cited

U.S. PATENT DOCUMENTS 3,987,042 10/1976 Gueremy et al. .................... 544/43

Primary Examiner—Richard L. Raymond
Attorney, Agent, or Firm—McAulay, Fields, Fisher, Goldstein & Nissen

[57] ABSTRACT

Quarternized derivatives of mequitazine, particularly 3-(10-H-phenothiazine-methyl)-1-methyl-1-azoniabicyclo [2.2.2]-octane iodide, show powerful anti-bronchospastic activity if administered by inhalation.

6 Claims, No Drawings

PHENOTHIAZINE COMPOUNDS WITH ANTI-BRONCHOSPASTIC ACTIVITY AND PHARMACEUTICAL COMPOSITIONS CONTAINING THEM

FIELD OF THE INVENTION

The present invention relates to compounds having anti-bronchospastic activity and to the pharmaceutical compositions containing them.

BACKGROUND OF THE INVENTION

The therapy of obstructive bronchopneumopathy with substances having antimuscarine activity, known in folk medicine by the name of "cigarette for asthma" and containing Datura stramonium, has been again recently studied under the modern form of the predosed aerosol. As a matter of fact, the vagal reflex bronchial obstruction in the pathogenesis of the obstructive diseases of the respiratory organs has a role much more important than that previously believed. A number of noxious factors abounding in industrial society ($SO_2$, sufuric acid, ammonia, exhaust gas, cigarette smoke and others) reflexively causes an increase in the tone of the bronchial muscles, which can be prevented by antimuscarine agents. Thus at the present time antimuscarine agents, administered mainly by inhalation, are becoming the therapeutical agents of choice (anta-agonists, theophillinic, corticosteroids, disodium chromoglycate).

The present invention relates to novel anti-bronchospastic compounds to be administered by inhalation and which compose some quaternized derivatives of 10-(1-azobicyclo-[2.2.2.]-oct-3-yl-methyl)-10-H-phenothiazine (i.e. mequitazine).

Mequitazine is an anti-histamine drug, whose activity takes place through a histamine antagonism at the level of the $H_1$ receptors and is consequently indicated for the symptomatic treatment of a number of allergic states (hay-cold, vasomotor rhinitis, nettle-rash, itch, allergic conjunctivities, Quincke oedema, allergic eczema, insect stings), in the same manner as classic anti-histaminic drugs, among which it is characterized according to published papers by a long lasting action and by a scarcity of side effects of the CNS level.

In only one paper (Med. et Hyg. 41, 7, 1983) is there a report of the protective action of mequitazine towards the bronchial hyperreactivity of patients affected by asthma, under well defined conditions.

Like effects have been previously claimed for other anti-histaminic drugs, such as promethazine, mepyramine, clopheniramine and clemastine, which however in the classic textbook of pharmacology (Goodman and Gilman, the Pharmacological Basis of Therapeutics, 627, McMillan N.Y. 1980) are defined as "singularly inefficacious in the bronchial asthma".

UK Patent specification No. 1250534 claims mequitazine and its analogues as possible antihistaminic, antidepressant and psycholeptic agents for oral, parenteral and rectal administration. Some homologues of mequitazine, including their salts, are described in this patent and its scope is extended also to the related quaternary ammonium derivatives, none of which however is described under the chemical and/or pharmacological aspect.

SUMMARY OF THE INVENTION

It has been now found that some quaternary ammonium derivatives of mequitazine show a powerful anti-bronchospastic activity.

The comparison of this property with the starting compound has shown that the subject quaternized derivatives, mixtures thereof, and particularly one of them, i.e. 3-(10-H-phenothiazin-methyl)-1-methyl-1-azoniabicyclo[2.2.2]-octane iodide, exhibit a powerful anti-bronchospastic activity whereas mequitazine itself is very slightly active or even inactive.

As a matter of fact, in a test of the spasm induced by methacholine in the isolated trachea of guinea pig, the aforesaid compound is 1000 times more active than free mequitazine and in a test of the bronchospasms induced by acetylcholine aerosol in the awake guinea pig, in which mequitazine is inactive up to essentially subtoxic doses, the same above compound exhibited a remarkable power.

Lastly, in pharmacological tests in which the administration by inhalatory route was used, it was observed that from one side the anti-bronchospastic activity of the above quaternized derivative is 20 times higher than that of mequitazine, and from the other side that the absorption through this route of the same compound is at least 24 times lower, whereby the greater power of the subject compound with respect to the mequitazine is enhanced by the possibility of using, by inhalatory route, high dosages without causing side effects of systemic type.

As matter of fact, switching from mequitazine to the related quaternary ammonium derivatives causes, from a pharmacodynamic point of view, a very high increase of the anti-muscarine activity at the tracheo-bronchial level and much less at the level of other organs, as well as an increase, also evident although less relevant, of the antagonism of other mediators of bronchospasm, i.e. of histamine, serotonine and $PGF_2$ alpha, and of the myolitic activity; from a pharmacokinetic point of view it causes a very remarkable reduction of the absorption by inhalatory and oral route, which may be explained on the basis of the chemical and physical properties of the compounds of the present invention, without prejudice but on the contrary with an enhancement of the anti-bronchospastic activity which takes place upon inhalation.

Owing to this simultaneous modification of the pharmacodynamic and pharmacokinetic properties, the compounds of the present invention and particularly the above indicated compound are thus definitely distinguished from mequitazine and the greater difference is seen in the therapeutical uses, since the subject compounds are useful as novel anti-bronchospastic agents of prevailingly anti-muscarine useful type, mainly for inhalatory administration in the treatment of bronchial obstructive forms, in a therapeutical field in which mequitazine, as all the other anti-histamine compounds, in view of the above described properties and of those found by the Applicant, would not have a useful application.

The compounds of the present invention and particularly the above cited compound, available in a pharmaceutical preparation suitable for inhalatory administration as predosed aerosol, are thus characterized as drugs capable of acting topically on the muscles of the respiratory organs and of avoiding side affects of the systemic type at the therapeutical dosages owing to their very poor absorption by inhalatory and oral route (since also the oral absorption is important, provided that most of a product administered by inhalatory route is in fact received in the digesting tract).

The present invention thus relates to some ammonium quaternary derivatives of 10-(1-azabicyclo[2.2.2]oct-3-yl-methyl-10-H-phenothiazine (mequitazine) and particularly to 3-(10-H-phenothiazin-methyl)-1-methyl-azoniabicyclo[2.2.2]-octane iodide (I), 3-(10-H-phenothiazin-methyl)-1-ethyl-1-azoniabicyclo[2.2.2]-octane iodide (II), 3-(10-H-phenothiazin-methyl)-1-propyl-1-azoniabicyclo[2.2.2]-octane iodide (III), 3-(10-H-phenothiazin-methyl)-1-isopropyl-1-azoniabicyclo[2.2.2]-octane iodide (IV), and mixtures thereof in the treatment of obstructive bronchial pneumopathies. The present invention further relates to pharmaceutical compositions characterized by containing, as the active ingredient, one of the aforesaid compounds and by being in a form suitable for the inhalatory administration in proper dosages of the same compounds.

The above properties are confirmed by the studies carried out by the Applicant, as hereinafter reported, which mainly relate to the compound (I) of the above listed compounds and which form the subject of the present invention. In the bronchospasm of the anestetized guinea pig induced by ACh i.v. (Konzett-Roessler method) the compound (I), administered by venous route, exhibited an activity 13 times higher than that of mequitazine (ED 50 of 51 and 674 nmol/kg respectively), and, administered by inhalatory route, an activity 20 times higher (ED50 of 26 and 499 nmol/kg respectively).

The absorption of compound (I) by inhalation in comparison with mequitazine has been studied by comparing their sistemic effects with intravenous and inhalatory routes. The inhibiting effect of the tested compounds on the hypotension induced by ACh i.v. in the anestetized rat has been used. The activity of the compound (I) and of the mequitazine by i.v. route, expressed as ED 50, is respectively 1.17 and 4.01 $\mu$mol/kg.

By inhalatory administration, the ED 50 of mequitazine is 4.06 $\mu$mol/kg, whereby a complete absorption through this route is demonstrated, whereas for the compound (I) of the invention it can not be calculated (25 $\mu$mol/kg), thus demonstrating that compound (I) is very poorly absorbed.

In the bronchospasm induced by ACh aerosol in the awake guinea pig the compound (I) of the invention, administered by venous route, did show an intense and dose-dependent activity (ED 50: 0.41 $\mu$mol/kg i.v.), whereas mequitazine is practically inactive even at doses 20 times higher.

In the bronchospasm induced by histamine aerosol in the awake guinea pig the activity of the compound (I) of the invention i.v. administered (ED 50=0.12 $\mu$mol/kg) is about 5 times higher than that of mequitazine (ED 50=0.65 $\mu$mol/kg).

In the spasm induced in the isolated trachea of guinea pig by methacholine, histamine and KCl, respectively, the compound (I) (IC 50: $3.4 \times 10^{-8}$, $7.4 \times 10^{-8}$ and $3.8 \times 10^{-5}$M respectively) has shown an activity greater than mequitazine (IC 50: $4.0 \times 10^{-5}$, $3.7 \times 10^{-6}$ and $1.1 \times 10^{-4}$M respectively), by 1200, 50 and 3 times.

In the isolated ileum of guinea pig the compound (I) is respectively 7, 15, 6 and 2 times more active than mequitazine in inhibiting the spasm induced by ACh, histamine, serotonine and PGF$_2$ alpha.

In an acute toxicity test in the mouse, the LD 50 of compound (I) by i.v. route is 3.15 mg/kg, whereas that of mequitazine is 23.7 mg/kg. On the contrary by oral route the LD 50 of compound (I) is about 700 mg/kg and that of mequitazine is about 350 mg/kg, which demonstrates that the absorption of compound (I) by oral route is very modest.

The compounds of the present invention and their of preparation methods are disclosed in the following examples.

EXAMPLE 1

3-(10-H-phenothiazin-methyl)-1-methyl-1-azoniabicyclo[2.2.2]-octane iodide 6.5 g (0.02 moles) of 10-(1-azobicyclo[2.2.2]-oct-3-yl-methyl)-10-H-phenothiazine (mequitazine) dissolved by heating in 85 ml of acetonitrile are added with 3 g (0.021 moles) of methyl iodide and the resulting solution is heated in a closed vessel at 50° C. for 16 hours. After prolonged cooling of the reaction mixture a colorless crystalline precipitate is separated which is filtered and further purified by crystallization from 80 ml of methanol giving 6.5 g of the desired compound in the form of colorless crystals having an m.p. 224°–6° C. thin layer chromatographic analysis (TLC), (eluants butanol 6, acetic acid 2, water 2) indicates that it is a pure compound ($R_f$ about 0.3). Elemental and spectrographic analysis give results in agreement with the theoretical structure.

EXAMPLE 2

3-(10-H-phenothiazin-methyl)-1-ethyl-1-azoniabicyclo[2.2.2]-octane iodide 6.5 g of mequitazine, 85 ml of acetonitrile and 3.3 g of ethyl iodide are serially charged in a suitable vessel and heated to 50° C. for 40 hours.

The reaction solvent is removed by distillation under vacuum, leaving a viscous residue which, taken up with ether and filtered, gives a solid straw-yellow product which is purified through crystallization from 300 ml of ethanol, 6 g of the desired product are obtained in form of ivory coloured crystals having an m.p. 260°–2° C.

The TLC analysis indicates that pure product is obtained (Rf 0.35). Elemental and spectrographic analysis give results in agreement with the expected structure.

EXAMPLE 3

3-(10-H-phenothiazin-methyl)-1-propyl-1-azoniabicyclo[2.2.2]-octane iodide 6.5 g of mequitazine and 3.6 g of propyl iodide, in 85 ml of acetonitrile, are reacted according to the method of example 2, and a straw-yellow solid product thus precipitated from the reaction mixture is purified by crystallization from 50 ml of methanol, giving 4.2 g of the expected product in form of ivory crystals having m.p. 269°–72° C.

The TLC analysis indicates that it is a pure compound (Fr 0.4).

Elemental and spectrographic analysis give results in agreement with the expected structure.

EXAMPLE 4

3-(10-H-phenothiazin-methyl)-1-isopropyl-1-azoniabicyclo[2.2.2]-octane iodide 6.5 g of mequitazine and 3.6 g of 2-iodo-propane, in 85 ml of acetonitrile, are reacted according to the method of example 2, and by subsequently using the same isolating process, a yellow solid is obtained which is purified by crystallization from 70 ml of methanol, to yield 5.9 g of the expected product in the form of ochre-yellow crystals, having m.p. 230°–2° C.

The TLC analysis indicates that a pure compound is obtained (Rf 0.35).

Elemental and spectrographic analysis give results in agreement with the expected structure.

EXAMPLE 5

3-(10-H-phenothiazin-methyl)-1-methyl-1-azoniabicyclo[2.2.2]-octane methylsulfate 1.10 g (3.4 moles) of mequitazine in 10 ml of benzene are treated with 0.76 g (6 moles) of dimethylsulfate and the resulting solution is kept of irrescent for 24 hours. The crystalline precipitate is collected by filtration and purified by crystallization from methanol giving 1.4 g of the expected product in form of colorless crystals, having m.p. 211°–15° C.

The TLC and elemental analyses give results in agreement with the expected structure.

EXAMPLE 6

This example illustrates a pharmaceutical composition suitable for the administration of proper doses of the compounds illustrated in the example 1 to 5.

compound (I): 0.05 g
polysorbate-80: 1.50 g
D-glucitol: 15.00 g
aqueous vehicle and propellant based on halogenated hydrocarbons: enough to 100.00 g

EXAMPLE 7 compound (I): 0.05 g
sodium dioctylsulfosuccinate: 0.10 g
aqueous vehicle and propellant based on nitrogen: enough to 100.00 g These pharmaceutical compositions, contained in a nebulizer with dosing valve, permit the administration of single measured doses of 50 to 200 µg of active compound.

1 to 3 daily administrations are suitable for the conditions treated.

I claim:

1. A compound selected from the group consisting of:
3-(10-H-phenothiazin-methyl)-1-methyl-1-azoniabicyclo[2.2.2]-octane iodide,
3-(10-H-phenothiazin-methyl)-1-ethyl-1-azoniabicyclo[2.2.2]-octane iodide,
3-(10-H-phenothiazin-methyl)-1-propyl-1-azoniabicyclo[2.2.2]-octane iodide,
3-(10-H-phenothiazin-methyl)-1-isopropyl-1-azoniabicyclo[2.2.2]-octane iodide,
3-(10-H-phenothiazin-methyl)-1-methyl-azoniabicyclo[2.2.2]-octane methyl sulphate, and mixtures thereof.

2. Pharmaceutical composition for the treatment of obstructive bronchial pneumopathies, for inhalatory administration, containing, as the active ingredient a compound according to claim 1, together with the usual vehicles and excipients.

3. Pharmaceutical composition according to claim 2, characterized in that said compound is 3-(10-H-phenothiazin-methyl)-1-methyl-1-azoniabicyclo[2.2.2]-octane iodide.

4. A method of treating a bronchospastic condition which comprises administrating a pharmaceutical composition of claim 2, said administration being effected by inhalation.

5. The method of claim 4 wherein the administration takes place by means of a nebulizer permitting the administration of single measured doses of 50 to 200 micrograms of active compound 1 to 3 times daily.

6. The method of claim 5 wherein the composition is the composition of claim 3.

* * * * *